US007700195B2

(12) United States Patent
Airoldi et al.

(10) Patent No.: US 7,700,195 B2
(45) Date of Patent: Apr. 20, 2010

(54) CUTTING TOOL AND PROCESS FOR THE FORMATION THEREOF

(75) Inventors: Vladimir Jesus Trava Airoldi, Sao Paulo (BR); Evaldo Jose Corat, Jacarei (BR); Joao Roberto Moro, Campinas (BR)

(73) Assignee: Fundacao De Amparo A Pesquisa Do Estado De Sao Paulo, Sao Paulo-Sp (BR)

( * ) Notice: Subject to any disclaimer, the term of this patent is extended or adjusted under 35 U.S.C. 154(b) by 0 days.

(21) Appl. No.: 10/480,209

(22) PCT Filed: Jun. 7, 2002

(86) PCT No.: PCT/BR02/00078

§ 371 (c)(1),
(2), (4) Date: Dec. 10, 2003

(87) PCT Pub. No.: WO02/100612

PCT Pub. Date: Dec. 19, 2002

(65) Prior Publication Data

US 2004/0137230 A1    Jul. 15, 2004

(30) Foreign Application Priority Data

Jun. 8, 2001    (BR)    .................................... 0103109

(51) Int. Cl.
*B32B 27/14*    (2006.01)
*C23C 16/02*    (2006.01)
(52) U.S. Cl. .......................... 428/408; 51/307; 51/309; 407/119; 427/249.1; 427/307; 428/174; 428/469; 428/698

(58) Field of Classification Search ................. 428/174, 428/408, 469, 698; 51/307, 309; 427/307, 427/249.1; 407/118, 119; 433/165, 86
See application file for complete search history.

(56) References Cited

U.S. PATENT DOCUMENTS

| 3,956,826 A | 5/1976 | Perdreaux, Jr. |
| 4,330,278 A | 5/1982 | Martin |
| 4,505,676 A | 3/1985 | Gonser |

(Continued)

FOREIGN PATENT DOCUMENTS

BR    9500117    12/1996

(Continued)

OTHER PUBLICATIONS

Broges et al "Dental diamond burs made with a new technology" J Prosthet Dent. 199 Jul.; 82(1) p. 73-79.*

(Continued)

*Primary Examiner*—Archene Turner
(74) *Attorney, Agent, or Firm*—Darby & Darby P.C.

(57) ABSTRACT

A cutting tool and process for the formation thereof. The cutting tool comprises a basic body (1) presenting an active end portion (2) coated with a diamond film obtained by the CVD growth technique, having superficial accidents (10) that are arranged and dimensioned to produce a substantial increase of the seating area for the diamond film and an increased degree of mechanical interference with the latter. This invention refers to the cutting tool above and to the process of obtaining said tool, to be generally used for cutting, drilling, abrading and trimming, and particularly to be coupled to ultrasonic systems.

43 Claims, 4 Drawing Sheets

U.S. PATENT DOCUMENTS

| | | | |
|---|---|---|---|
| 4,707,384 A | | 11/1987 | Schachner et al. |
| 4,764,434 A | * | 8/1988 | Aronsson et al. ............. 428/408 |
| 5,011,515 A | * | 4/1991 | Frushour ..................... 51/307 |
| 5,022,801 A | | 6/1991 | Anthony et al. |
| 5,054,246 A | * | 10/1991 | Phaal et al. ................. 407/118 |
| 5,139,372 A | | 8/1992 | Tanabe et al. |
| 5,142,785 A | | 9/1992 | Grewal et al. |
| 5,232,568 A | | 8/1993 | Parent et al. |
| 5,236,740 A | * | 8/1993 | Peters et al. ........... 427/249.13 |
| 5,299,937 A | * | 4/1994 | Gow .......................... 433/165 |
| 5,355,969 A | * | 10/1994 | Hardy et al. ................ 175/432 |
| 5,376,444 A | | 12/1994 | Grotepass et al. |
| 5,379,854 A | * | 1/1995 | Dennis ........................ 51/307 |
| 5,431,239 A | * | 7/1995 | Tibbitts et al. .............. 175/428 |
| 5,469,927 A | * | 11/1995 | Griffin ....................... 175/432 |
| 5,558,789 A | * | 9/1996 | Singh ......................... 427/307 |
| 5,662,720 A | * | 9/1997 | O'Tighearnaigh ............ 51/309 |
| 5,688,557 A | * | 11/1997 | Lemelson et al. ...... 427/249.14 |
| 5,814,149 A | | 9/1998 | Shintani et al. |
| 5,836,765 A | | 11/1998 | Hickok et al. |
| 6,042,463 A | * | 3/2000 | Johnson et al. ............... 51/309 |
| 6,042,886 A | | 3/2000 | Matthee et al. |
| 6,164,968 A | * | 12/2000 | Feine .......................... 433/86 |
| 6,199,645 B1 | * | 3/2001 | Anderson et al. ........... 175/426 |
| 6,508,649 B2 | | 1/2003 | Gratz ......................... 433/142 |
| 6,547,562 B2 | * | 4/2003 | Kumar ....................... 433/165 |
| 6,641,395 B2 | * | 11/2003 | Kumar et al. ............... 433/165 |
| 6,722,883 B2 | * | 4/2004 | Gorokhovsky .............. 433/166 |

FOREIGN PATENT DOCUMENTS

| | | |
|---|---|---|
| EP | 0 628 642 A1 | 12/1994 |
| EP | 0 787 820 A2 | 8/1997 |
| EP | 0 860 515 A1 | 8/1998 |
| SU | 563280 | 6/1977 |
| SU | 837610 | 6/1981 |
| WO | WO 96/26303 | 8/1996 |
| WO | WO 00/29178 | 5/2000 |

OTHER PUBLICATIONS

Fan et al "Adhesion of diamond films on Ti-6Al-4V alloys" Surface and Coatings Techn 91 (1997) 32-36.*

Vandenbulcke et al "Two step process for improved diamond deposition on titanium alloys at moderate temperature". Appl. Phys. Lettt. 72 (4) Jan. 26, 1998.*

Patent Abstracts of Japan, vol. 017, No. 176 (C-1045), Apr. 6, 1993 & JP 04333577 A (Asahi Dalyamondo Kougiyou KK), Nov. 20, 1992.

Patent Abstracts of Japan, vol. 1995, No. 06, Jul. 31, 1995 & JP 07068425 A (Fujitsu Ltd.), Mar. 14, 1995.

F. Deuerler et al., "Pretreatment of Substrate Surface for Improved Adhesion of Diamond Films on Hard Metal Cutting Tools," *Diamond and Related Materials*, vol. 5, No. 12, Dec. 1, 1996, pp. 1478-1489.

* cited by examiner

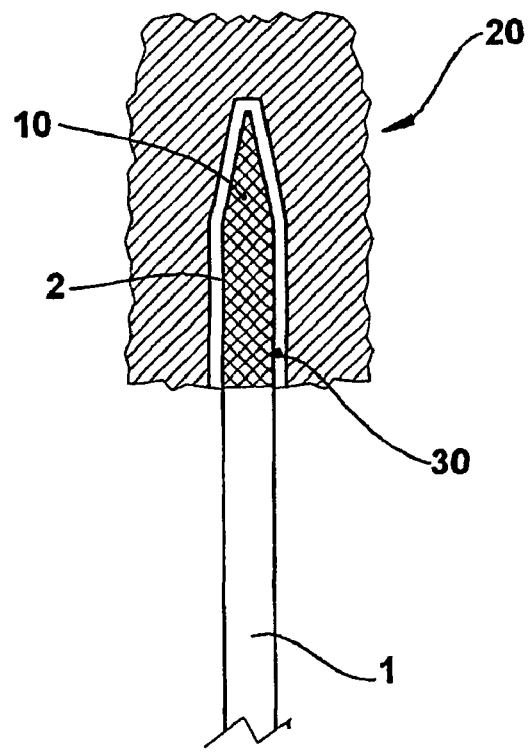
FIG.7
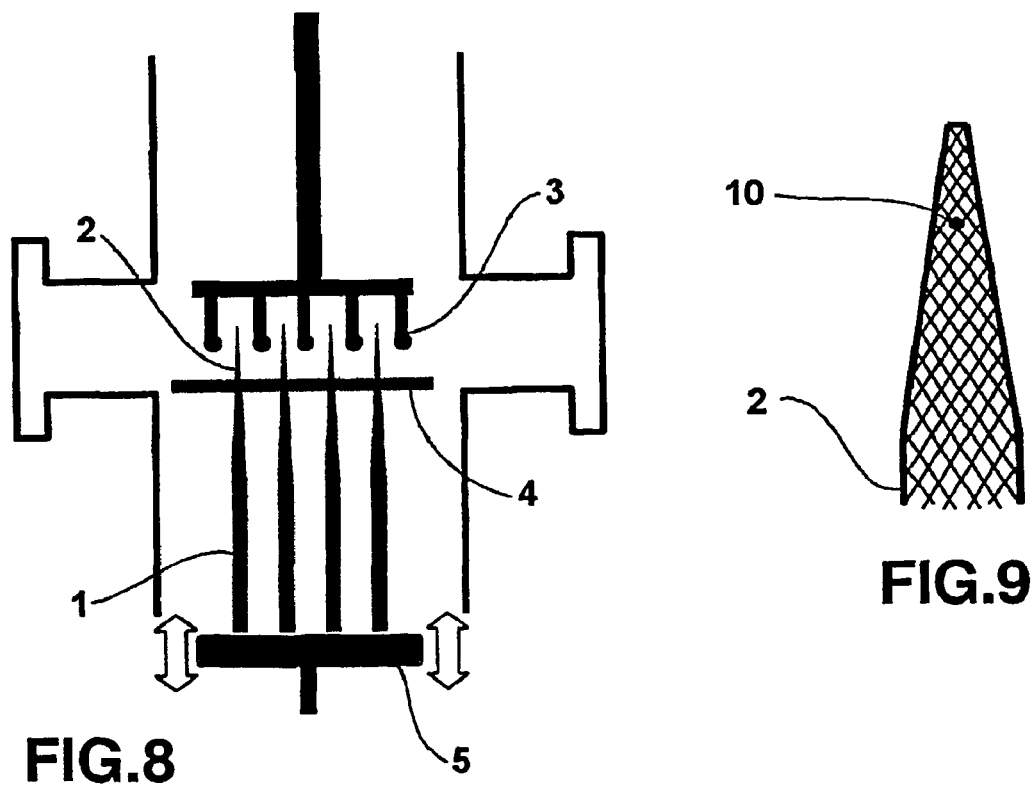
FIG.8
FIG.9

CUTTING TOOL AND PROCESS FOR THE FORMATION THEREOF

FIELD OF THE INVENTION

The present invention refers to a cutting tool and to a process for the formation of said tool by using the technology of Chemical Vapor Deposition (CVD) diamond growth, hereinafter denominated CVD diamond and, more specifically, to a tool and a process for the formation thereof, to be used in ultrasonic equipments of the type generally used for cutting, drilling, abrading and trimming any kind of surface made of materials, such as ceramic, glass, bone, dentine, nitrides, carbides, marble, granite, etc., and particularly for cutting hard materials.

BACKGROUND OF THE INVENTION

The use of ultrasound in applications such as cutting, drilling, abrading, trimming and cleaning has been known for a long time. Its advantages are also well known, mainly the capacity of machining materials in regions of difficult access, where the use of rotary machining processes or those processes requiring high amplitude of displacement is not possible.

By using mechanical vibrations of low amplitude and relatively high frequency, an important characteristic of the ultrasonic processes of cutting, drilling, abrading, trimming and cleaning is the processing of only the material under the direct action of the tool, with minimum influence on the nearby regions, resulting in high precision. Since ultrasound propagates in metallic materials, it is possible to make tools with various shapes and access angles, which permits not only the processing in the form given by the tool, but to do so in regions of difficult access (SU1456098; U.S. Pat. Nos. 4,330,278; 4,505,676).

Ultrasonic tools have a special design that takes into account the ultrasound propagation in the tool material and the determination of a stationary wave pattern of the mechanical vibrations. Generally, a tool is designed to have maximum vibration in its active region and minimum vibration on the holders (WO200029178). As to the tool material, it is important for said material to be a good ultrasound transmitter and have high ultimate strength to ultrasound. This last characteristic of the tool material is highly important, since the processing speed depends on the ultrasound intensity and the maximum intensity of use may be limited by the ultimate strength of the tool material to ultrasound.

The active region of the ultrasonic tool depends on the material to be processed. However, in a significant number of applications, the use of metallic tips from the own base material of the tool is sufficient. In cleaning processes, one can make tips from materials based on resins or plastics. For the cutting, drilling, abrading and trimming processes, the material of the active tip of the tool is required to be harder or more wear resistant than the material to be processed. Thus, the use of active tips of materials different from that of the tool body, or with a coating of harder material on the material of the tool body is a very important development. Nevertheless, these alternatives are limited to the fact that the interface, which connects the hard material to the tool body, must withstand the ultrasound action without breaking.

Particularly for the processing of very hard materials, or those requiring special care, such as stones, ceramics, glasses, bones, dentine, nitrides, carbides, etc., the ultrasonic processes of cutting, drilling, abrading and trimming are usually indicated, but there is a limitation as to the obtainment of tools with active tips having a hardness and strength suitable for such applications. Alternatively, where possible, abrasive powders under the action of less hard tools and also diamond coated tools are used. However, conventional diamond coating processes are inadequate to use in ultrasonic tools. The agglutination of diamond powder with various grain sizes, by electrochemical deposition of nickel, diamond-metal and diamond-resin composites, which are widely used techniques for producing conventional tools, is inadequate to ultrasonic tools, as the diamond grains are easily released from said tools during operation thereof, rapidly exposing the metal of said tool to the surface of the material being processed. In order to overcome these limitations, special alloys using different metals were developed to allow a better wettability of the diamond grains and consequently provide a diamond powder agglutination that is more resistant to ultrasound (SU563280; SU837610). With such modifications it was possible to extend the lives of these tools for some types of applications, without however reaching a desired adequate level.

While CVD diamond coatings have been employed for manufacturing tools, there are no references as to their application in ultrasonic tools (U.S. Pat. Nos. 5,232,568; 5,142,785; 5,376,444; 5,139,372; 4,707,384; 5,022,801; WO09626303; BR9500117).

In some specific constructions of an ultrasonic cutting tool, it is desirable to have the basic body of said tool in molybdenum, since this is a material in which the ultrasound propagates quite well and has high ultimate strength to ultrasound. Also, it is a material that, under certain conditions, allows diamond growth of good quality and relative adherence.

However, in the diamond growth environment, the molybdenum is extensively carburized and transformed into molybdenum carbide, which is highly susceptible to rupture by ultrasound action. Moreover, the adherence that is normally obtained by conventional methods between the diamond film and molybdenum is insufficient for the interface to withstand the ultrasound action, of medium intensity, without breaking.

SUMMARY OF THE INVENTION

Thus, it is an object of the present invention to provide a cutting tool of the type used in materials of high hardness, which allows the formation of at least one active end portion in CVD diamond presenting high resistance and durability, in order to withstand, for example, the ultrasound action.

It is a further object of the present invention to provide a cutting tool of the type mentioned above, which allows the growth, at least on its active end portion, of a CVD diamond layer independently of the material that forms said tool, said layer presenting a substantial adherence to the material that forms said tool.

It is still a further object of the present invention to provide a process for the formation of a cutting tool of the type mentioned above to be used in high hardness materials.

These and other objects are attained by a cutting tool comprising a basic body having an active end portion coated with a diamond film obtained by the CVD growth technique, comprising superficial accidents that are arranged and dimensioned to produce a substantial increase of the seating area for the diamond film and an increased degree of mechanical interference with the latter.

The above cutting tool is obtained by means of a process for the formation of a cutting tool comprising the steps of:

a—providing the active end portion with superficial accidents that are arranged and dimensioned to produce a substantial increase of the seating area for the diamond film and an increased degree of mechanical interference with the latter;

b—cleaning both physically and chemically the surface of the active end portion; and c—submitting the active end portion to nucleation of the diamond film.

BRIEF DESCRIPTION OF THE DRAWINGS

The present invention will be described below, based on the appended drawings, in which:

FIG. 7 illustrates, schematically, a longitudinal sectional view of an active end portion having a layer of DVD diamond grown on said active end portion by the process of the present invention;

FIG. 8 illustrates, schematically and in a front view, a diagram of a CVD diamond growth reactor of the type used in the process for forming the cutting tool of the present invention;

FIG. 9 illustrates, schematically and in an enlarged view, an active end portion of a basic body of a cutting tool to be formed in accordance with the present invention.

DETAILED DESCRIPTION OF THE INVENTION

Figure 1:
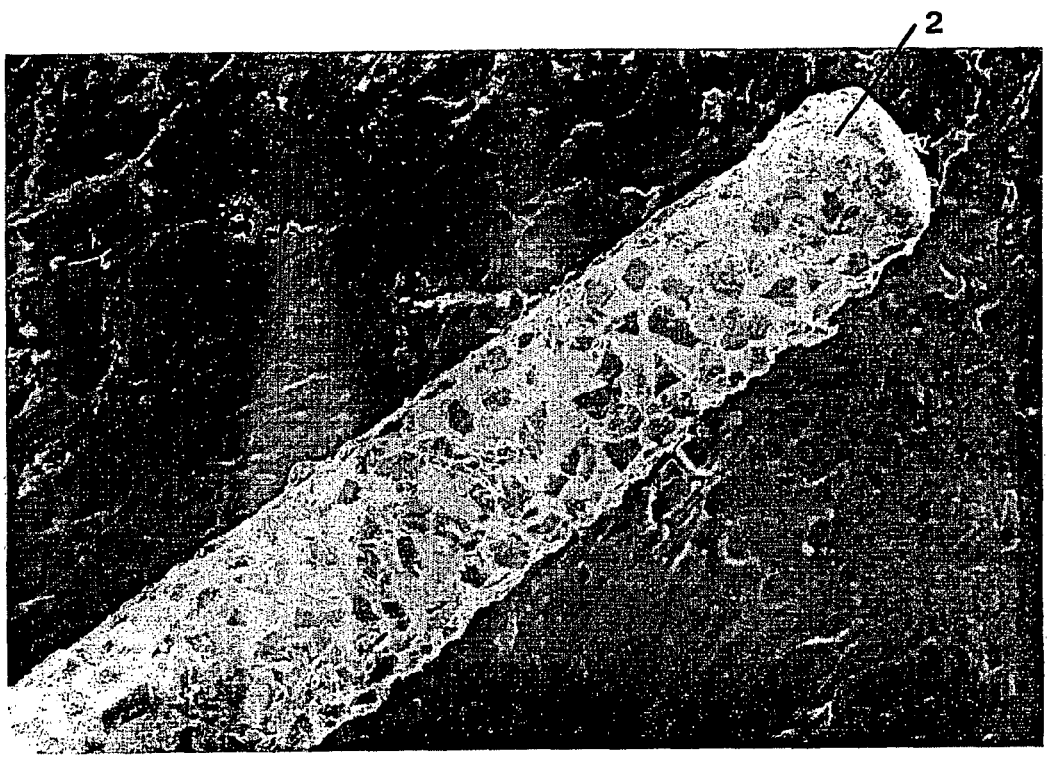
FIG. 1 illustrates, schematically, a view of an active end portion of a tool, with a cylindrical shape and constructed in accordance to the prior art.

The present invention will be described in relation to a cutting tool, particularly to be used with ultrasound and of the type used for cutting, abrading and other related activities in a hard material, said tool presenting a basic body 1 having an active end portion 2, which is coated with a diamond film (thin or thick) obtained by the CVD growth technique and which defines, after its growth on the active end portion 2, a diamond layer in a single piece.

To produce ultrasonic tools covered with a CVD diamond layer, it is necessary to take into account the following factors: the tool material needs to be a good ultrasound transmitter and have high ultimate strength to ultrasound; it has to be adequate to CVD diamond deposition, withstanding the extremely adverse conditions of the deposition environment and allowing growth of a diamond film of good quality and good adherence; after deposition of the CVD diamond film, this material should preserve its properties regarding ultrasound application; the adherence between the CVD diamond coating and the material of the basic body 1 of the tool should be sufficiently high to withstand the ultrasound action in the interface, without the coating suffering delamination.

According to the present invention, the cutting tool comprises, at least on its active end portion 2, superficial accidents 10 that are arranged and dimensioned to produce a substantial increase of the seating area for the CVD diamond film and an increased degree of mechanical interference with the latter.

The tool of the present invention is formed by a process comprising the steps of: providing the active end portion 2 of a basic body 1, that is made of a metallic material adequate to cut hard materials, with the superficial accidents 10; cleaning both physically and chemically the surface of said active end portion 2, for example by using an ultrasonic bath with degreasing solvents, in order to remove from said surface the debris generated during manufacture and handling; and submitting the active end portion 2 to nucleation, for example in a CVD diamond film growth reactor (FIG. 8), for forming a single piece diamond coating.

In a way of carrying out the present invention, the physical cleaning occurs independently of the chemical cleaning, in which, for example, the active end portion is submitted to a degreasing operation, preferably in a bath with a degreasing solvent. In the present embodiment, said step of physically and chemically cleaning occurs by submitting the active end portion 2 to an ultrasonic bath with degreasing solvents.

The provision of superficial accidents 10 is achieved by means of a mechanical process for preparing the surface of the active end portion 2, by making dense knurls or scores, which promote mechanical interlocking of the grown CVD diamond film and an increase of the area where this thin or thick film will be grown.

The preparation step that follows the provision of the superficial accidents 10 is obtained by means of a process for treating the surface in ultrasonic baths with solvents, ionic sub-implantation in the power range, for example, from 10 eV to about 2000 eV, with atoms of at least one of the atom groups of nitrogen and/or carbon, oxygen, and hydrogen, it being possible to form different compounds, depending on the material of the basic body 1.

In a way of carrying out the present invention, prior to the step of diamond film nucleation, there is provided an additional step of submitting the active end portion 2 to an operation of removing the oxides from said active end portion 2, for example by submitting the latter to a cleaning operation in an atomic hydrogen rich environment. Such removal of oxides allows increasing the adherence of the diamond film to be grown on said active end portion 2.

The mechanical processes of dense knurling and/or scoring can be identical to any type of basic body 1, while the cleaning operation and the cleaning process in a hydrogen environment can be different, depending on the material of said basic body 1.

In an embodiment of the present invention, when the material of the active end portion 2 does not allow adequate growth of the diamond film, the process of forming the present cutting tool provides an additional step, after the step of physically and chemically cleaning described above, in which said active end portion 2 is submitted to a surface treatment with ion bombardment, with an intensity and time that are calculated to chemically transform the surface of the active end portion 2, making it adequate to nucleation, said -bombardment being achieved, for example, through ionic sub-implantation by ionic immersion or by direct current discharge.

In the preparation step with ionic sub-implantation by ionic immersion, the latter may occur in a power range, for example, from about 0.2 keV to 100 keV. This step occurs due to the need of enhancing the adherence and uses, for example, ions of nitrogen and/or carbon and/or hydrogen, with possible formation of composites. This treatment increases the adherence between the CVD diamond coating and the material of the basic body 1 of the tool, inhibiting diffusion of both the carbon and hydrogen to the inside of said basic body 1, protecting the material thereof in order not to lose its characteristics of ultrasound propagation and ultimate strength to ultrasound during the CVD diamond deposition process, due to the inhibition of the formation of an extensive carbide or hydrogen layer when said material is, for example, steel or alloys thereof, molybdenum or alloys thereof, niobium or alloys thereof, and titanium or alloys thereof.

With the step of ionic sub-implantation, the surface of the active end portion 2 and a layer of the latter immediately under said surface aggregate a modified layer, preferably ions of nitrogen, carbon and hydrogen that improve the adherence of the diamond film to be grown on the active end portion 2.

Figure 6:
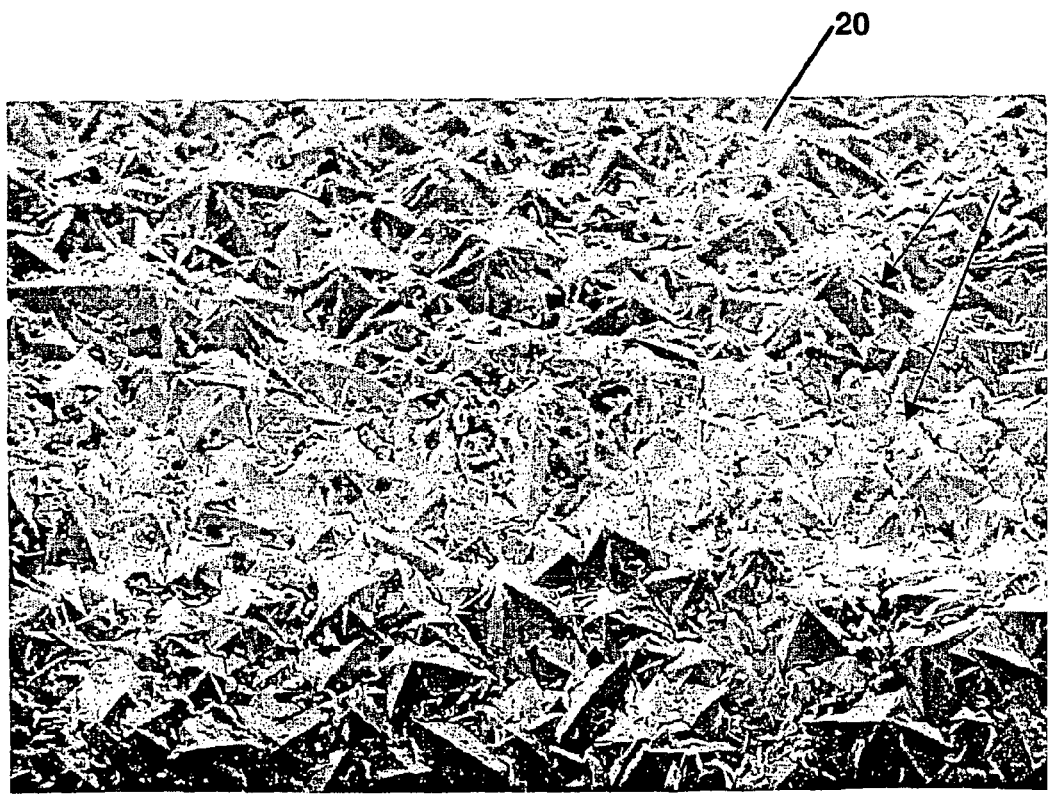
FIG. 6 illustrates, schematically, an enlarged view of part of the active end portion illustrated in FIG. 5.

The process of forming cutting tools of the present invention occurs, for example, in the interior of an adequate CVD growth reactor (FIG. 8), in which, between a set of basic bodies 1, filaments 3 are placed, each basic body 1 being supported by a respective substract carrier 4 seated on a base 5, which is for example vertically movable (or rotatively movable, in the case of annular tools of the type illustrated in FIG. 6), in order to allow a relative displacement of the basic bodies 1 in relation to the filaments 3.

FIG. 9 illustrates an active end portion 2 of a basic body 1 presenting the superficial accidents 10, onto which will be performed the CVD diamond growth, in accordance with the present invention.

Controlling the growth of the diamond grains regarding, for example, uniformity throughout the extension of the active end portion 2 of each basic body 1, is achieved by controlling some parameters, such as the distance between the filaments 3 and the basic bodies 1.

The growth parameters are fundamental to guarantee a rough surface, with the predominant obtainment of the crystallographic structure (111), whose fully coalesced grains are of convenient size for abrasive use by the energetic action of the ultrasound.

The tools prepared in accordance with the present invention dispense any type of special welding, since the diamond is already retained to the material of the active end portion 2 of the basic body 1 with the desired dimensions.

Figure 2:
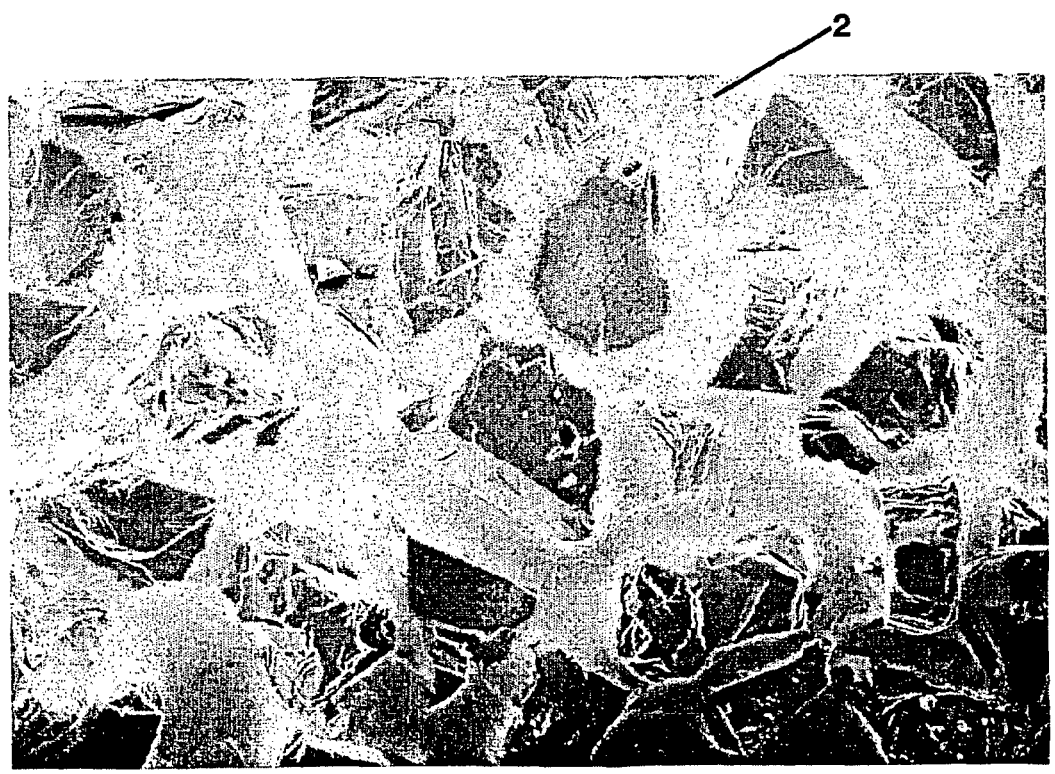
FIG. 2 illustrates, schematically, an enlarged view of part of the active end portion illustrated in FIG. 1.
Figure 3:
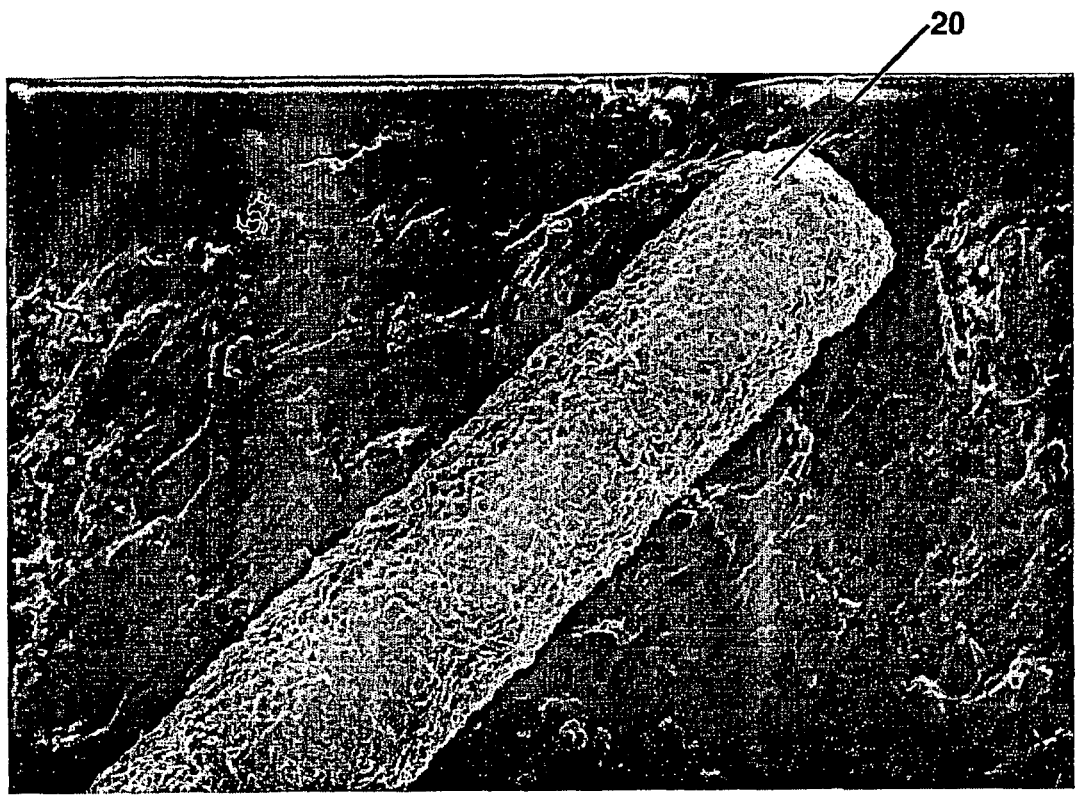
FIG. 3 illustrates, schematically, a view of an active end portion of a tool, with a cylindrical shape and formed with CVD diamond by the process of the present invention.
Figure 4:
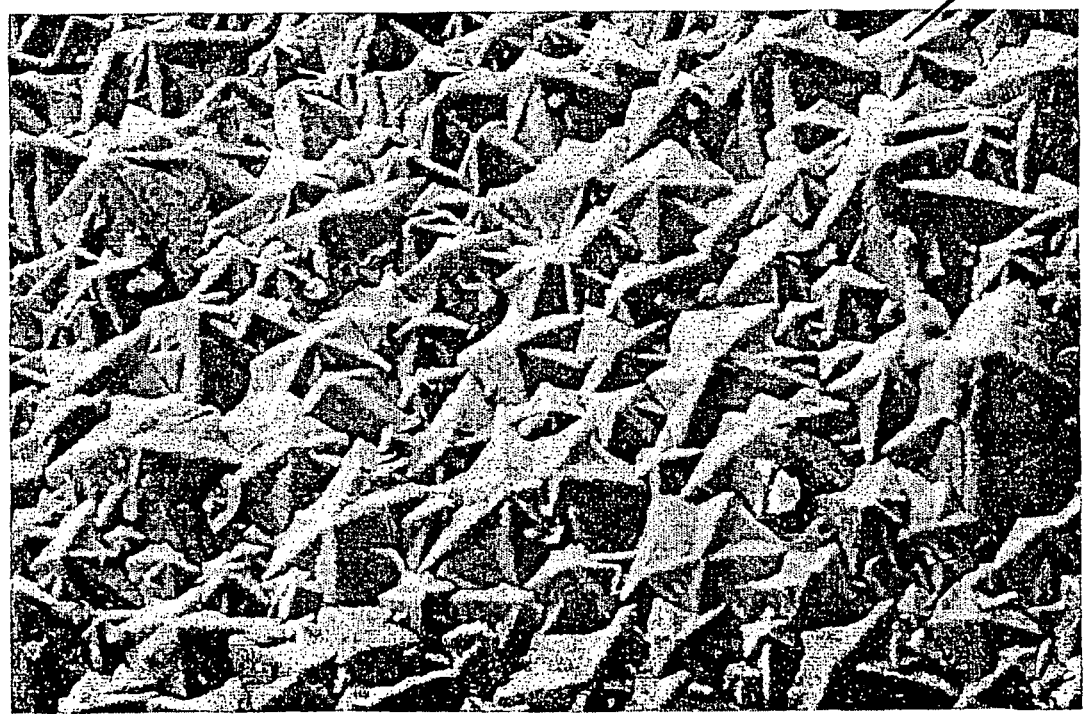
FIG. 4 illustrates, schematically, an enlarged view of part of the active end portion illustrated in FIG. 3.

The solution of the present invention results in a tool, whose active end portion 2 presents high durability, about 30 times more durable than an active end portion 2 obtained by the prior art technologies, such as that schematically illustrated in FIGS. 1 and 2, in which the active end portion 2 receives a diamond coated layer formed by galvanizing diamond grains, defining a structure with the deficiencies mentioned above.

The present solution allows obtaining different forms of active end portions 2 to be employed where the use of rotary tools is not permitted, or at least not advisable, as for example, in dental treatment (U.S. Pat. No. 3,956,826) with retro-instrumentation and/or where access to rotary systems (U.S. Pat. No. 5,875,896) or those systems requiring movements to remove material by abrasive process is not possible.

In addition, the cutting tools obtained by the present invention may be used to substitute the already existing rotary tools, since the cutting speed thereof is also relatively high and they present a better finish in relation to the rotary devices, besides guaranteeing less trauma to the material being treated, whatever the material under the action of the ultrasonic device.

These tools, whose drilling and/or trimming action is made by means of ultrasound, may have rectilinear or angular forms (cylindrical, conical, inverted conical, spherical, flame shaped, annular, etc.) providing an abrading or drilling intervention in regions of difficult access, in any type of application, either in dental and/or medical surgeries, or in industrial processes.

The tool of the present invention has the following advantages: it is substantially less prejudicial to the material under intervention, as it produces less impact than the rotary movement; it presents a better final finish for abrasion or drilling, since, by controlling the amplitude of the ultrasound vibration, the preparation of the active end portion 2 and the grain size of the CVD diamond, the roughness defined for the active end portion 2 by the superficial accidents thereon is controlled; in case of being employed in the odontological field, it avoids the metals from contacting the human tissue, or any material to be trimmed; it does not produce intense noise like that produced by high rotation motors; it presents a better finish of surface treatment, i.e., with less roughness; it is cleaned more easily after use and, due to producing less impact, as compared to the drilling and/or trimming processes by means of rotary devices, it causes less trauma to the tissue being treated, since the cut or perforation or a simple trimming is more precise and less aggressive, causing no fissures around the region to be treated. In the case of the annular shaped devices used for cutting and/or trimming mainly in glasses, ceramics, stones, etc., all these advantages are equally present.

Figure 5:
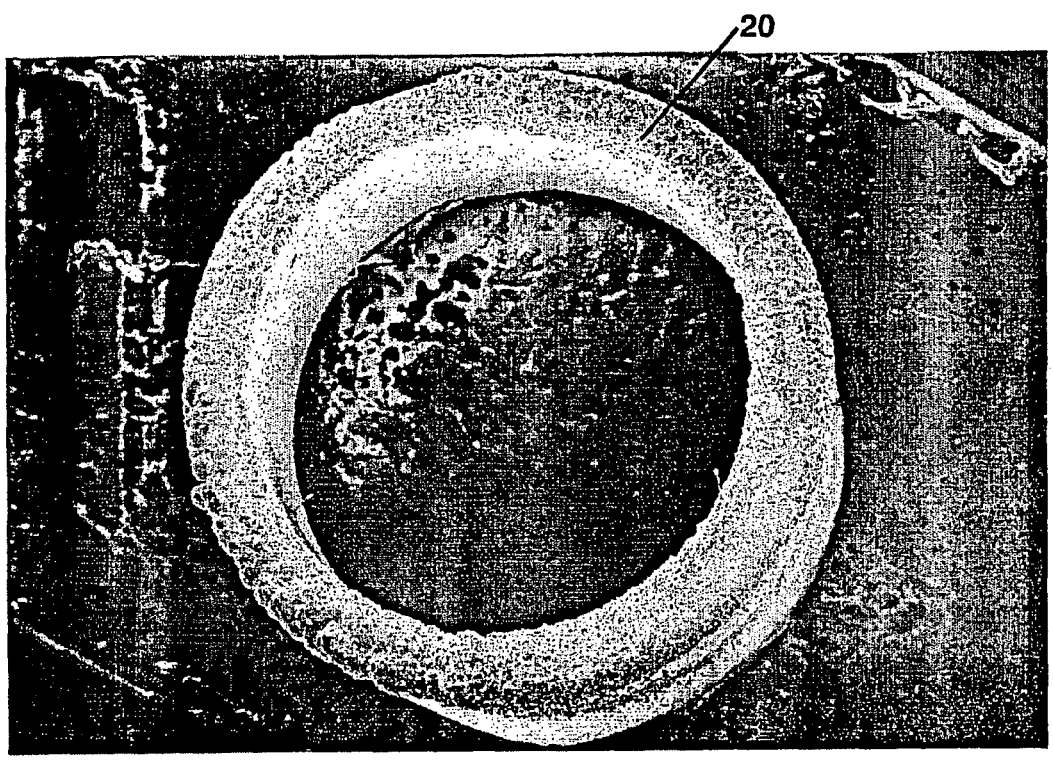
FIG. 5 illustrates, schematically, an active end portion, of annular shape and formed with CVD diamond in accordance with the present invention.

In the case of using annular burrs in CVD diamond (FIGS. 5 and 6) with drilling techniques that use ultrasound, it should be pointed out that, with the present solution, it is not necessary to use any additional powder of abrasive material for trimming, like in the conventional technique, which makes the process absolutely clean and without introducing any other drilling agent.

In the conventional solutions, the tools, which are used for the same purposes, both in the odontological and medical fields, and in the industrial perforations of glasses, ceramics, etc., and which are manufactured with diamond powder (galvanically welded, such as illustrated in FIGS. 1 and 2, or by other process, to a support material) allow the diamond powder to be released relatively easily, leading the surface being treated to contact the support metal, resulting in a very short useful life.

The cutting tools of the present invention (FIGS. 3-6) in which the diamond layer grown by the CVD technology forms a single piece in the active end portion 2 of the basic body 1 of said tools, differ from those conventionally obtained, providing a long useful life, with no diamond release and without permitting the surface being treated to be exposed to the support material. The characteristic of an active end portion 2 in the form of a single piece diamond layer, which is entirely continuous and, at the same time, rough, with a grain size which, on being small, assures desirable finish and desirable precision on drilling and trimming. Such characteristic of being formed in a single piece and with a substantially uniform grain size is shown in FIGS. 3-6.

The rough surface is obtained by adequately controlling the growth parameters of CVD diamond, such as the size of the grains that may be controlled to grow, for example, from between 20 to 100 micrometers in an active end portion 2 provided, for example, with superficial accidents 10 produced thereon prior to the deposition of a CVD diamond film layer that reproduces said superficial accidents, or it may be also obtained, for example, on an intermediate layer 30 that is made of a material presenting the characteristics of transmission and strength and also compatibility with diamond growth, and which is provided in the basic body 1, when the material of the latter is not compatible with diamond growth, like the steels, and when the step of submitting the active end portion 2 to the ionic sub-implantation described above is not carried out. The provision of said intermediate layer 30 allows the surface of the active end portion 2 to be capable of receiving nucleation of the diamond film thereon.

While the molybdenum and its alloys (as well as other materials) present properties to work with ultrasound, they are inadequate for diamond deposition and/or have their properties altered when submitted to high diamond growth temperatures, in an environment containing high concentration of hydrogen and carbon, as in the present CVD diamond growth technique. In the diamond growth environment, the molybdenum is extensively carburized, being transformed into molybdenum carbide, which is very susceptible to rupture by ultrasound action. Also, the adherence that is normally obtained by the conventional methods between the diamond film and the molybdenum is insufficient for the interface to withstand the ultrasound action, of moderate intensity, without suffering rupture.

In view of the above, the present invention provides a solution presenting an intermediate layer 30 that allows for an adherent deposition of the CVD diamond film, as well as a process for recovering the properties after said deposition.

According to the present invention, the intermediate layer 30 presents, externally, superficial accidents 10 that produce a substantial increase of the seating area of the diamond film and an increased degree of mechanical interference with the latter.

In a possible embodiment, the intermediate layer 30 reproduces the superficial accidents 10 of the active end portion 2, said intermediate layer 30 being, for example, a film that is deposited on the active end portion 2. In another embodiment, the intermediate layer 30 is treated, after deposition thereof on the active end portion 2, in such a way as to present external superficial accidents 10 as well, which are obtained by an adequate technique and designed to produce a substantial increase of the seating area for the diamond film and an increased degree of mechanical interference with the latter.

According to the present invention and on being the tool of the type to be used with ultrasound, the material of the basic body 1 is made of a metallic material presenting good ultrasound transmission, high ultimate strength to ultrasound, capacity to preserve said properties, and adequacy to CVD diamond growth. In the case of a basic body 1 being made of a selected material, this intermediate layer 30 can be a silicon carbide film.

In the case of tools to be used with ultrasound, whose amplitude and frequency are calculated according to the specific use, the material of the basic body 1 is also specified as a function of the ultrasound frequency and power.

In accordance with the present invention, the material of the basic body 1 of the present cutting tool can be further selected from one of the groups consisting of steels and alloys thereof, molybdenum and alloys thereof, niobium and alloys thereof, and titanium and alloys thereof.

In order to obtain the desired abrading and cutting characteristic, for example, the present invention controls the characteristics of the superficial accidents 10 produced on the active end portion 2 and which are formed, for example, by knurling and/or scoring, and/or by jetting with sand, glass, particulate material, etc., and/or by trimming the surface of said active end portion 2.

According to the present invention, this preparation of the active end portion 2 allows, not only to increase the interface area of diamond deposition, but also increase the area of mechanical interference that retains the CVD diamond layer grown on said active end portion 2.

It should be pointed out that the level of adherence obtained between the CVD diamond film and the material of the basic body 1 of the present tool is such as to permit operations of cutting, drilling, abrading and trimming, which were not possible before with the conventional ultrasonic tools.

The invention claimed is:

1. An ultrasonic operated cutting tool comprising:
   a basic body presenting an active end portion having a surface with a diamond film obtained by CVD growth technique, said basic body comprising superficial accidents that are arranged and dimensioned to produce a substantial increase of the seating area for the diamond film and an increased degree of mechanical interference with the latter, and
   a coating layer formed between the basic body and the diamond film, the coating layer comprising a modified layer that comprises a surface of said active end portion and a layer immediately under said surface of the active end portion and presenting, externally, the superficial accidents, said modified layer being an ionic modified layer presenting at least one of the ions defined by nitrogen, carbon and hydrogen, at least one of said ions having a controlled diffusion into the basic body and inhibiting the diffusion of carbon and hydrogen into the basic body, and said basic body being a metallic material having good ultrasound transmission, high ultimate strength to ultrasound, adequacy to diamond film growth and being adapted to preserve said properties after said diamond film growth.

2. The cutting tool as set forth in claim 1, wherein the superficial accidents are obtained by at least one of the forms defined by knurling and scoring.

3. The cutting tool as set forth in claim 1, wherein the superficial accidents are obtained by at least one of the forms defined by trimming and jetting.

4. The cutting tool as set forth in claim 1, wherein the material of the basic body is selected from the group consisting of steels and alloys thereof, molybdenum and alloys thereof, niobium and alloys thereof, and titanium and alloys thereof.

5. The cutting tool as set forth in claim 1, characterized in that the active end portion has an annular cross-section.

6. The cutting tool as set forth in claim 1, wherein the ionic modified layer is formed by ionic sub-implantation.

7. An ultrasonic operated cutting tool comprising:
   a basic body presenting an active end portion submitted to a treatment for preparing its surface with ion bombardment with an intensity and time that are calculated so as to chemically transform said surface and make it adequate to diamond film nucleation and having a surface with a diamond film obtained by CVD growth technique, said basic body comprising superficial accidents that are arranged and dimensioned to produce a substantial increase of the seating area for a coating layer and an increased degree of mechanical interference with the latter,
   wherein said coating layer comprises an intermediate layer between the basic body and the diamond film in the form of a film that is deposited on the active end portion, and presents, externally, the superficial accidents, and said basic body being a metallic material having good ultrasound transmission, high ultimate strength to ultrasound, adequacy to diamond film growth and being adapted to preserve said properties after said diamond film growth.

8. The cutting tool as set forth in claim 7, wherein the intermediate layer reproduces the superficial accidents of the active end portion.

9. The cutting tool as set forth in claim 7, wherein the film is made of silicon carbide.

10. A process for the formation of a cutting tool to be used in ultrasonic equipment comprising a basic body presenting an active end portion having a surface provided with a diamond film obtained by the CVD growth technique, the process comprising the steps of:
- a—providing a basic body consisting of a metallic material;
- b—providing a coating layer comprising a modified layer defined by a surface of said active end portion and by a layer immediately under said surface of said active end portion, said modified layer being an ionic modified layer presenting at least one of the ions defined by nitrogen, carbon and hydrogen, at least one of said ions having a controlled diffusion into the basic body and inhibiting the diffusion of carbon and hydrogen into the basic body;
- c—providing the active end portion with superficial accidents that are arranged and dimensioned to produce a substantial increase of the seating area for the diamond film and an increased degree of mechanical interference with the latter;
- d—cleaning both physically and chemically the surface of the active end portion; and
- e—submitting the active end portion to nucleation of the diamond film.

11. A process for the formation of a cutting tool to be used in ultrasonic equipment comprising a basic body presenting an active end portion having a surface provided with a diamond film obtained by the CYD growth technique, the process comprising the steps of:
- a—providing a basic body consisting of a metallic material;
- b—providing the surface of the active end portion with superficial accidents that are arranged and dimensioned to produce a substantial increase of the seating area for the diamond film and an increased degree of mechanical interference with the latter;
- c—submitting the active end portion to a treatment for preparing the surface with ion bombardment with an intensity and time that are calculated so as to chemically transform said surface and make it adequate to diamond film nucleation;
- d—providing an intermediate layer between the basic body and the diamond film, on the surface of the active end portion of the basic body;
- e—producing a substantial increase of the seating area of said intermediate layer for the diamond film and an increased degree of mechanical interference with the latter;
- f—cleaning both physically and chemically the surface of the active end portion; and
- g—submitting the active end portion to nucleation of the diamond film.

12. The process as set forth in claim 10, wherein the active end portion is submitted to one of the knurling and scoring processes.

13. The process as set forth in claim 11, wherein the active end portion is submitted to one of the knurling and scoring processes.

14. The process as set forth in claim 10, wherein the active end portion is submitted to one of the trimming and jetting processes.

15. The process as set forth in claim 11, wherein the active end portion is submitted to one of the trimming and jetting processes.

16. The process as set forth in claim 10 wherein the step of cleaning the active end portion includes submitting the active end portion to an ultrasound bath.

17. The process as set forth in claim 11 wherein the step of cleaning the active end portion includes submitting the active end portion to an ultrasound bath.

18. The process as set forth in claim 10 wherein the step of cleaning the active end portion includes a step of submitting the active end portion to a degreasing operation.

19. The process as set forth in claim 11 wherein the step of cleaning the active end portion includes a step of submitting the active end portion to a degreasing operation.

20. The process as set forth in claim 18, wherein the degreasing operation includes submitting the active end portion to a bath with degreasing solvents.

21. The process as set forth in claim 19, wherein the degreasing operation includes submitting the active end portion to a bath with degreasing solvents.

22. The process as set forth in claim 10, wherein the material of the basic body is selected from the group consisting of niobium and alloys thereof, and titanium and alloys thereof.

23. The process as set forth in claim 11, wherein the material of the basic body is selected from the group consisting of niobium and alloys thereof, and titanium and alloys thereof.

24. The process as set forth in claim 10, further comprising the step of submitting the active end portion to a treatment for preparing the surface with ion bombardment with an intensity and time that are calculated so as to chemically transform said surface and make it adequate to diamond film nucleation.

25. The process as set forth in claim 24, wherein the additional step is by preparation with ionic sub-implantation in the power range from about 10 eV to about 2000 eV.

26. The process as set forth in claim 11, wherein the ion bombardment step is by preparation with ionic sub-implantation in the power range from about 10 eV to about 2000 eV.

27. The process as set forth in claim 24, wherein the step of ion bombardment is by ionic immersion in the power range from about 0.2 keV to about 100 keV.

28. The process as set forth in claim 11, wherein the ion bombardment step is by ionic immersion in the power range from about 0.2 keV to about 100 keV.

29. The process as set forth in claim 27, wherein the ionic immersion is made with atoms of at least one of the elements selected from the group consisting of carbon, nitrogen, oxygen, and hydrogen.

30. The process as set forth in claim 28, wherein the ionic immersion is made with atoms of at least one of the elements selected from the group consisting of carbon, nitrogen, oxygen, and hydrogen.

31. The process as set forth in claim 29, wherein the step of ionic immersion includes submitting the active end portion to a direct current discharge.

32. The process as set forth in claim 30, wherein the step of ionic immersion includes submitting the active end portion to a direct current discharge.

33. The process as set forth in claim 31, wherein the direct current discharge is with one of the elements defined by nitrogen and carbon in a hydrogen environment.

34. The process as set forth in claim 32, wherein the direct current discharge is with one of the elements defined by nitrogen and carbon in a hydrogen environment.

35. The process as set forth in claim 11, including an additional step of reproducing, with the intermediate layer, the superficial accidents of the active end portion.

36. The process as set forth in claim 35, including an additional step of depositing on the active end portion a film defining the intermediate layer.

37. The process as set forth in claim 36, wherein the film comprises silicon carbide.

38. The process as set forth in claim 10, further comprising the step of submitting the active end portion to an operation to remove oxides from the surface thereof prior to the nucleation step.

39. The process as set forth in claim 11, further comprising the step of submitting the active end portion to an operation to remove oxides from the surface thereof prior to the nucleation step.

40. The process as set forth in claim 38, wherein the step of removing the oxides is obtained by submitting the active end portion to a cleaning operation in an environment with atomic hydrogen.

41. The process as set forth in claim 39, wherein the step of removing the oxides is obtained by submitting the active end portion to a cleaning operation in an environment with atomic hydrogen.

42. The process as set forth in claim 10, wherein the metallic material has good ultrasound transmission, high ultimate strength to ultrasound, adequacy to diamond film growth and being adapted to preserve said properties after said diamond film growth.

43. The process as set forth in claim 11, wherein the metallic material has good ultrasound transmission, high ultimate strength to ultrasound, adequacy to diamond film growth and being adapted to preserve said properties after said diamond film growth.

* * * * *